United States Patent [19]

Yabrov et al.

[11] Patent Number: 4,880,417

[45] Date of Patent: Nov. 14, 1989

[54] DEODORIZING AND SOUND MUFFLING ANAL PAD

[75] Inventors: Alexander A. Yabrov, Princeton; Michael Roitberg, Highland Park, both of N.J.

[73] Assignee: Biological Resistance, Inc., Princeton, N.J.

[21] Appl. No.: 109,152

[22] Filed: Oct. 16, 1987

[51] Int. Cl.⁴ .................................................. A61F 5/44
[52] U.S. Cl. ..................................... 604/355; 604/359; 604/379; 604/385.1; 604/393
[58] Field of Search ............... 604/355, 359, 393, 379, 604/327, 392, 385 R

[56] References Cited

U.S. PATENT DOCUMENTS

| | | |
|---|---|---|
| 2,024,145 | 12/1935 | Cline . |
| 2,629,381 | 2/1953 | Brown . |
| 2,682,875 | 7/1954 | Brown . |
| 2,742,042 | 4/1956 | Flanders . |
| 2,771,882 | 11/1956 | Leupold . |
| 2,858,830 | 11/1958 | Robins . |
| 2,964,039 | 12/1960 | Johnson, Jr. et al. . |
| 3,039,893 | 6/1962 | Banigan, Jr. et al. . |
| 3,103,930 | 9/1963 | Collett et al. . |
| 3,172,817 | 3/1965 | Leupold et al. . |
| 3,199,945 | 8/1965 | Stutz . |
| 3,294,090 | 12/1966 | Younger ........................... 604/385.1 |
| 3,563,242 | 2/1971 | Hedstrom ............................. 604/392 |
| 3,736,931 | 6/1973 | Glassman . |
| 3,897,782 | 8/1975 | Tunc ..................................... 604/364 |
| 4,053,053 | 10/1977 | Tumangday . |
| 4,060,450 | 11/1977 | Palazzolo et al. ..................... 428/531 |
| 4,182,335 | 1/1980 | Matrullo . |
| 4,195,634 | 4/1980 | DiSalvo et al. ........................ 604/359 |
| 4,237,591 | 12/1980 | Ginocchio ............................. 604/359 |
| 4,352,356 | 10/1982 | Tong ..................................... 604/393 |
| 4,405,326 | 9/1983 | Lenagham ......................... 604/385.1 |
| 4,505,707 | 3/1985 | Feeney ................................. 604/359 |
| 4,559,051 | 12/1985 | Hanson ............................. 604/385 R |
| 4,579,556 | 4/1986 | McFarland . |
| 4,589,876 | 5/1986 | Van Tillburg ........................ 604/393 |
| 4,624,666 | 11/1986 | DeRossett et al. ................... 604/379 |
| 4,662,877 | 5/1987 | Williams . |
| 4,668,230 | 5/1987 | Damico et al. . |
| 4,713,069 | 12/1987 | Wang et al. .......................... 604/382 |
| 4,722,936 | 2/1988 | Jacob ..................................... 424/19 |
| 4,753,648 | 6/1988 | Jackson ................................ 604/393 |

FOREIGN PATENT DOCUMENTS

| | | |
|---|---|---|
| 2552662 | 7/1984 | France . |
| 24523 | of 1906 | United Kingdom ................ 604/393 |
| 2165457 | 4/1986 | United Kingdom . |

OTHER PUBLICATIONS

James Casey, Pulp and Paper Chemistry and Technology, 1980, 97-98.

Primary Examiner—John D. Yasko
Assistant Examiner—Mark O. Polatta
Attorney, Agent, or Firm—Banner, Birch, McKie & Beckett

[57] ABSTRACT

An anal pad for preventing soiling of underwear due to undesired anal discharge. The anal pad includes a thin outer shell enclosing a semi-rigid shell. The semi-rigid shell may be a layer on one interior surface of the outer shell and it may also partially cover the opposite interior surface of the outer shell. An absorbing layer is located within the outer shell and the semi-rigid layer. The absorbing layer contains glycerin which absorbs hydrogen sulfide gas and the combination of the absorbing layer and the semi-rigid shell acts as a sound muffling camera so as to decrease the noise due to flatus. The absorbing layer is made of a light porous materials, the semi-rigid layer is made of compressed paper and the outer shell is made of a thin sheet of lignin paper. A layer of glue is provided on the outer surface of the anal pad for attaching it to a user's underwear.

7 Claims, 8 Drawing Sheets

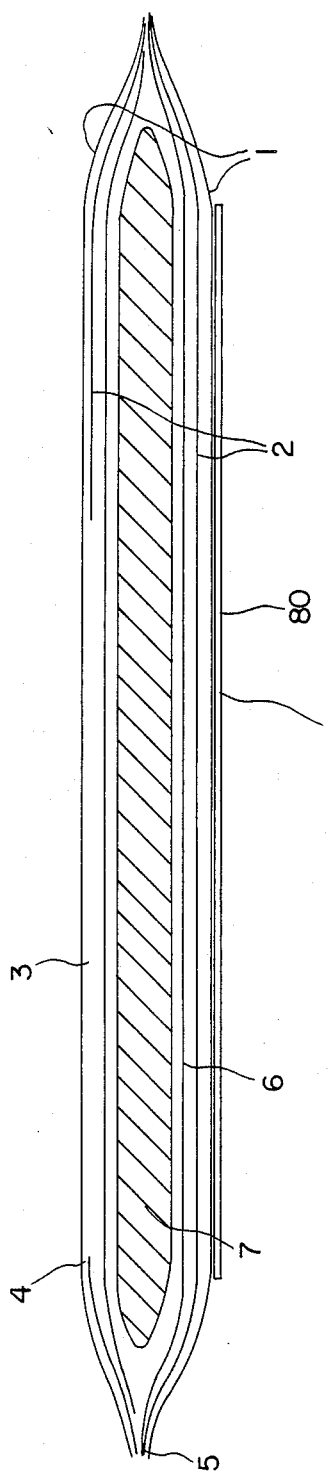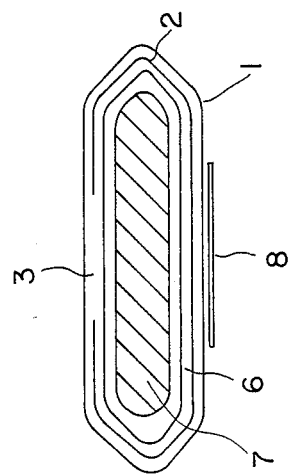

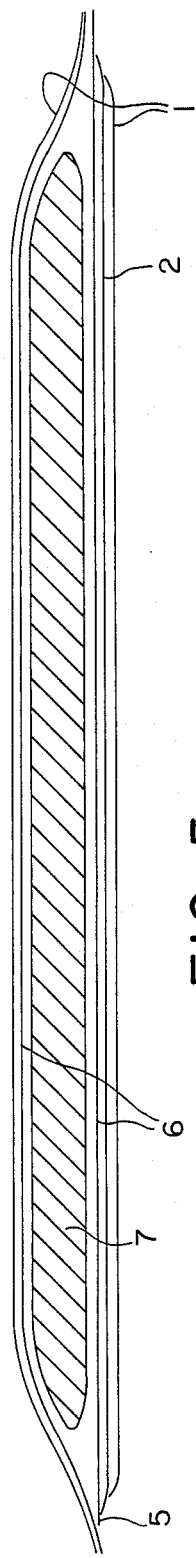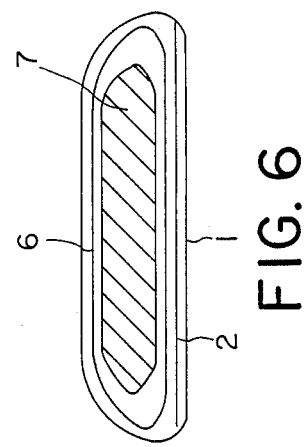

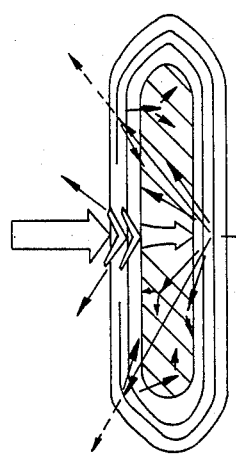
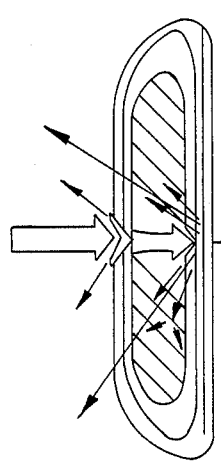

DEODORIZING AND SOUND MUFFLING ANAL PAD

BACKGROUND OF THE INVENTION

1. Field of Invention

This invention relates to the field of toiletry and individual hygiene, and more particularly, to a hygienic disposable anal pad.

2. Description of the Prior Art

Involuntary leakage of the content of the alimentary canal from the anus is prevented by the sphincter, a ringlike muscle band. Normally, the action of the sphincter alone is sufficient to prevent unwanted discharge. However, the vertical posture of the human body subjects the anal sphincter to a continuous stress. The gripping capacity of the sphincter deteriorates with age as a consequence of the general process of weakening of muscles. In addition, certain lifestyles and habits promote the weakening of the sphincter. For example, a sedentary lifestyle or an occupation which requires the lifting of heavy loads may cause this unwanted weakening. In addition, the sphincter is weakened in those who passively participate in anal intercourse as well as in women who suffer the descendence of pelvic organs after repeated deliveries. Local chronic processes such as diarrhea, constipation and hemorrhoids as well as any surgical operation in the sphincter, for example, the excision of hemorrhoids or a fissure, lead to the weakening of the sphincter and result in an insufficiency in the gripping capacity of the sphincter.

Weakening of the sphincter is a problem that affects a large number of people. Loss of control of the expulsion of gases and fecal material from the anus can result in social embarrassment and may be a source of infection.

U.S. Pat. No. 2,742,042 to Flanders discloses an anal napkin for use by people who suffer from minor uncontrollable anal discharges. The napkin is made of a flat piece of absorbing material such as cellulose fiber or absorbent cotton. In use, the napkin is placed between the buttocks and is shaped so as to conform to human anatomy. The napkin may also be impregnated with suitable deodorants if desired.

U.S. Pat. No. 4,182,335 to Matrullo discloses an anal filter which is made of fibrous material permanently fixed to a base layer. This device is folded over in use to form a wedge or V-shape and is also inserted between the buttocks. The anal filter of Matrullo is previous to the discharge of gas but impervious to the passage of excreta carried by the gas or remaining on the anus from a bowel movement. Thus, the anal filter protects underwear from possible soiling resulting from flatus.

Both the filter of Matrullo and the napkin of Flanders are directed to solving one particular problem, that is, to prevent soiling of underwear caused by a minor anal discharge or flatus, but are ineffective in dealing with a broad range of problems caused by incontinence. For example, the prior art does not provide for the mitigation of embarrassing noise caused by a flatus and does not capture and neutralize the offensive odor of expelled gases. In addition, the prior art is only partially effective in solving the problems which it addresses. Neither of the two devices can be reliably kept in the appropriate position, thus, the possiblity of soiling of the underwear is still present to a great degree. In addition, both devices are inconvenient because of the difficulty in maintaining the proper position.

SUMMARY OF THE INVENTION

It is an object of the present invention to provide an anal pad that effectively prevents soiling of a person's clothes due to an undesired anal discharge.

It is an object of the present invention to provide an anal pad that reduces the sound of a flatus.

It is an object of the present invention to provide for deodorization of the gases produced by flatus.

It is an object of the present invention to provide for an anal pad that is convenient, anatomically fitted, reliably positioned and does not interfere with ordinary movement of the person wearing it.

It is another object of the present invention to provide for deodorization of solid fecal matter absorbed by the pad.

It is another object of the present invention to provide for the prevention of irritation and inflammation of the tender mucous membranes and skin of the anal area.

It is also an object of the present invention to prevent dissemination of fecal microorganisms in the fecal matter so as to prevent infection of the urogenital organs such as cystitis, vulvovaginitis or nephritis.

These objects are accomplished by providing an anal pad which includes a thin outer shell wall that forms the entire outer surface of the anal pad. Within the outer shell is a semi-rigid inner shell made of compressed paper. The inner shell traps sound in the interior of the anal pad by reflecting sound from its interior surfaces. The inner shell lines the inner surface of the outer shell on one side thereof, and partially lines the inner surface on the other side so as to form a central gap beneath the outer shell. The outer shell may be made of a thin layer of lignin paper and the inner shell may be made of compressed paper, e.g., 5–7 layers of lignin paper. An absorbing layer, which may be made of cotton, rayon fiber or any other light porous material fills the interior of the anal pad. A second layer of thin lignin may be located within the inner shell so as to enclose an absorbing layer, or the absorbing layer may be located directly within the inner shell. The absorbing layer fills nearly the entire area within the inner shell and lies beneath the gap thereof. The absorbing layer absorbs sound reflected by the inner shell. The anal pad surface on the gap side is the inner surface and is located adjacent the anus of the user, while the outer surface is located next to the user's underwear. On the outer surface of the anal pad, there is an adhesive which is covered with removable paper which may be used to attach the garment to the underwear of the user.

Further objects, features and other aspects of this invention will be understood from the following detailed description of the preferred embodiments of this invention with reference to the Drawing Figures.

BRIEF DESCRIPTION OF THE DRAWINGS

FIG. 3 is a longitudinal cross-sectional view taken along the lines III—III in FIG. 1.

FIG. 4 is a lateral cross-sectional view taken along the lines IV—IV in FIG. 1.

FIG. 5 shows a longitudinal cross-sectional view of a second embodiment of the invention.

FIG. 6 shows a lateral cross-sectional view according to a second embodiment of the invention.

FIGS. 7a and 7b schematically show the sound muffling effect of the present invention.

DESCRIPTION OF THE PREFERRED EMBODIMENTS

Figure 1:
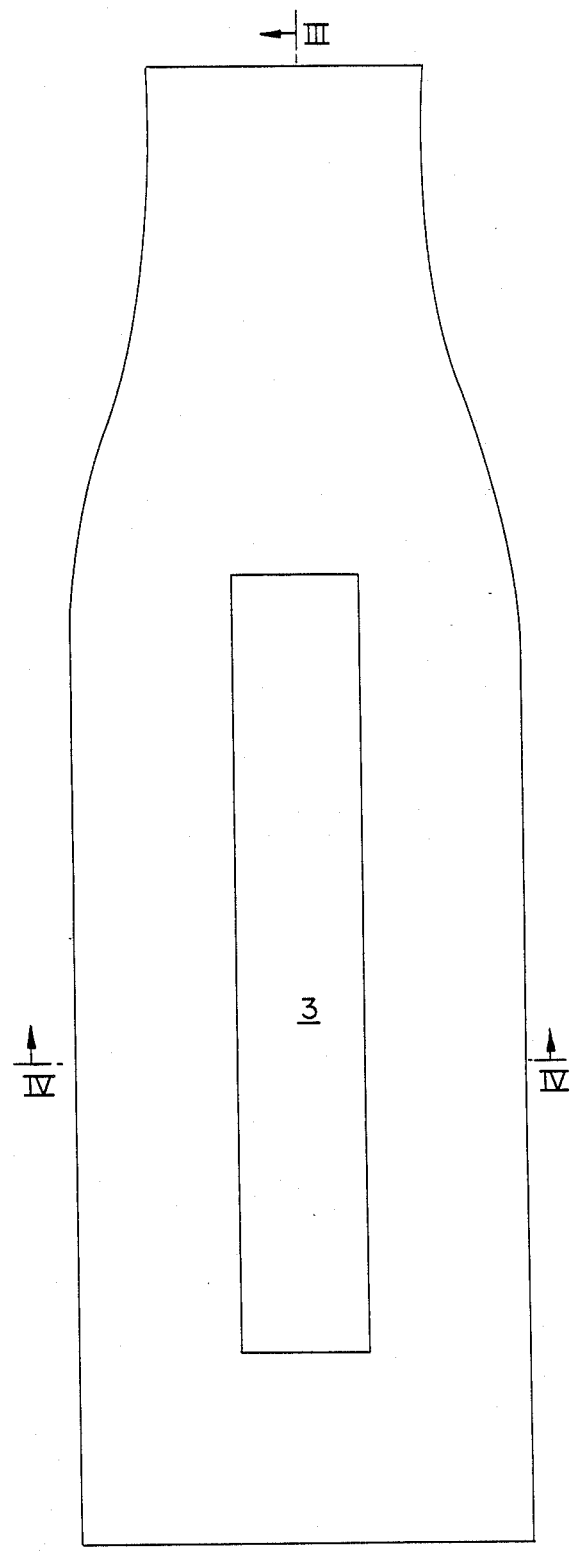
FIG. 1 is a top view showing the inner surface of the anal pad designed for use by men according to the present invention.
Figure 2:
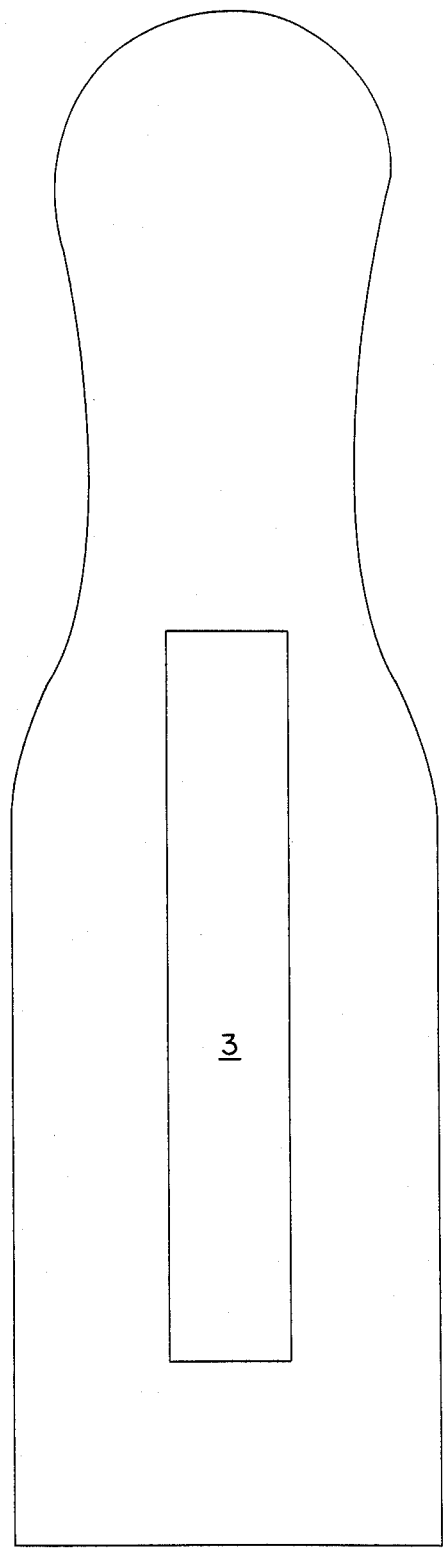
FIG. 2 is a top view showing the inner surface of the anal pad designed for use by women according to the present invention.

FIG. 1 shows a top view of the anal pad according to the present invention which is designed for use by men. Similarly, FIG. 2 shows the anal pad according to the present invention which is designed for use by women. The two pads are similar except for one end portion of the pad designed for women which is rounded while the same end in the pad designed for men has a straight edge. Additionally, total overall length of the pad is longer for women than it is for men. For example, the male pad may be 230 mm long while the female pad is 250 mm in overall length. These differences take into account the differences in genital structure between men and women.

Also shown in FIGS. 1 and 2 is central gap 3 which is formed in inner shell 2 beneath outer shell 1. In both pads, the central gap may be 120 mm long and 20 mm in width. Similarly, the width at one end of both pads is the same, for example, 70 mm. The exact dimensions of both pads are variable and can be changed as desired so that the present invention can be made to fit many different sizes. The exact numbers given above and below are for example only and do not necessarily restrict this invention to any one size.

As shown in FIGS. 3 and 4, the anal pad of the present invention includes outer shell 1 which defines the outer boundary of the pad. Outer shell 1 is made of one thin layer of, for example, lignin paper. Semi-rigid shell 2 is located within outer shell 1 and fully lines the interior surface of outer shell 1 on one side thereof, and partially lines the interior surface of outer shell 1 on the opposite side. The surface of the anal pad in which the interior surface of outer shell 1 is entirely lines is the outer surface and, in use, faces the user's underwear. The surface of the anal pad in which the interior surface of outer shell 1 is only partially lined is the inner surface, and, in use, faces the user's anus. Semi-rigid shell 2 is light and pliable and may be made of compressed paper. Semi-rigid shell 2 may be 1 mm thick and serves to reflect sound off of its interior surface.

At the inner surface of the pad, central slot 3 is formed where semi-rigid shell 2 does not entirely line the interior surface of outer shell 1. Central slot 3 serves as a window for the sound of flatus and is covered in its entirety by outer shell 1. Semi-rigid shell 2 has a further edge 4 defining the window on either side of central slot 3 in the first embodiment. The size and configuration of central slot 3 may vary as necessary and may be 120 mm long and 20 mm in width. These measurements have been experimentally shown to be efficacious in trapping the sound.

An absorbing layer 7 is located entirely within semi-rigid shell 2 and fills the interior space of the anal pad. Optionally, absorbing layer 7 may be entirely enclosed within inner layer 6, the combination being located within semi-rigid shell 2. Inner layer 6 may be made of a thin layer of lignin paper. Absorbing layer 7 may be 3–9 mm thick and is preferably made of cotton, rayon fiber or any other light and porous material. Absorbing layer 7 serves as a sound trapping filling of the anal pad. Absorbing layer 7 also serves to trap soiling matter and is impregnated with a deodorant. Absorbing layer 7 absorbs odorous gas which is reflected from the interior surfaces of the anal pad.

An adhesive material 8 is covered by removable paper 80 for attaching the anal pad to the underwear of the user. The width of this layer may be 40 mm and it is applied to the outer surface of the anal pad on an exterior surface of outer shell 1. The overall optimal thickness of the pad may be 6–7 mm. A thin layer of impermeable material, for example, polyethylene (not shown) may be inserted between absorbing layer 7 and inner layer 6 if desired to modify the anal pad so that it will absorb liquids as well.

It is known that hydrogen sulfide gas, $H_2S$ is the substance which contributes most to the offensive odor of the flatus. However, $H_2S$ dissolves readily in glycerin, therefore, the deodorant used in absorbing layer 7 includes glycerin as the active substance, along with fragrance. Of course, any other appropriate material may also be used as desired in addition with glycerin.

To prepare the deodorant, one teaspoon full of glycerin is dissolved in 50 ml of 95% ethyl alcohol. The ratio between ethyl alcohol and glycerin should be between 10:1 and 20:1. This solution is then poured on cotton wool or any other material which is to be used as the absorbing layer until it is completely soaked. A small amount of fragrance may either be added to the solution or sprinkled on the soaked absorbing layer. The absorbing layer is then left until most of the alcohol evaporates, a process which takes several hours. Since glycerin absorbs water and the fragrance tends to evaporate, the pad should be wrapped in water-tight paper or plastic as soon as possible after the alcohol evaporates. It should be noted that although glycerin is widely used in the toiletry industry, it is mostly used for its hydroscopic properties. It is a novel feature of the present invention to make use of glycerin for the neutralization of the odor caused by hydrogen sulfide gas.

A second embodiment of the anal pad according to the present invention is shown in FIGS. 5 and 6 in which semi-rigid shell 2 is a single layer. In this second embodiment, semi-rigid shell 2 does not extend around absorbing layer 7 to partially line the interior surface of outer layer 1 at the inner surface of the anal pad. Thus, no central slot 3 is formed. In all other respects, the second embodiment of the invention is identical to the first embodiment shown in FIGS. 3 and 4. As can be seen in FIGS. 3 and 5, in both embodiments the ends of outer shell 1, inner layer 6 and semi-rigid shell 2 are joined together at two edges 5 of the pad.

FIGS. 7a and 7b schematically show the sound muffling effect of the pad according to the first embodiment and second embodiment, respectively. In FIG. 7a, it can be seen that the pad traps the sound due to the sound reflecting from the interior surface of semi-rigid shell 2 and being scattered within the anal pad. The scattered sound is absorbed by absorbing layer 7, either on its first pass through or after being reflected from semi-rigid shell 2. Sound which is not absorbed on any pass through absorbing layer 7 is further absorbed after being reflected by the overhang of semi-rigid shell 2. With respect to FIG. 7b, it can be seen that much of the sound is reflected and absorbed in absorbing layer 7 even without the overhang of semi-rigid shell 2. FIG. 7b is a simpler embodiment than FIG. 7a, but it has been shown that it is still very effective with respect to its sound muffling capacity.

Figure 8A:
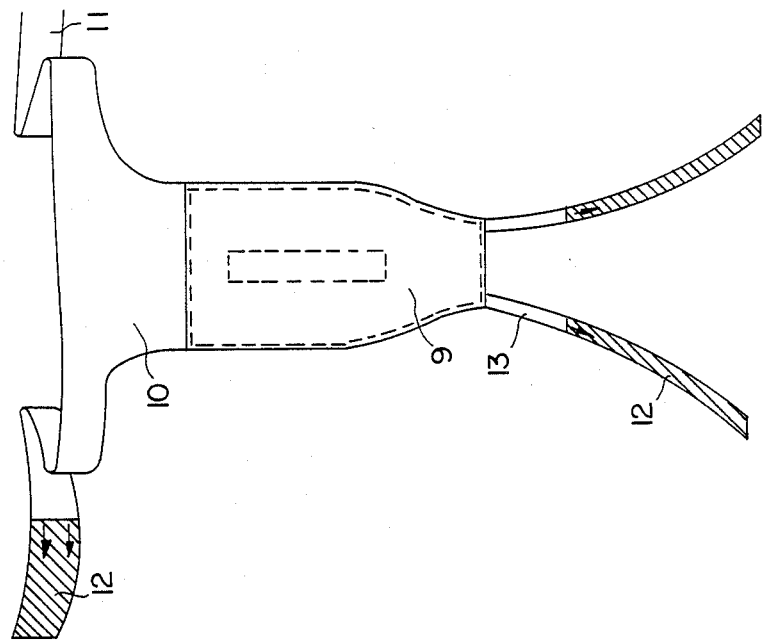
FIGS. 8a–8c show another embodiment of the present invention which is provided with a waistband.
Figure 8B:
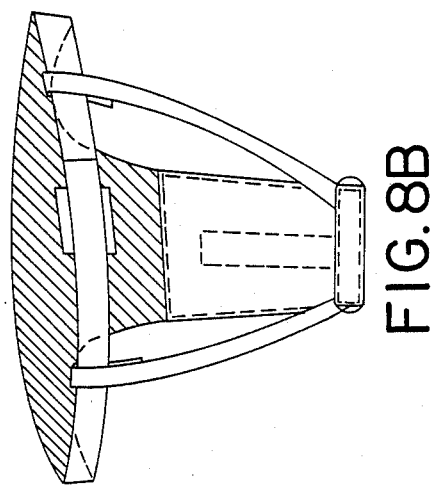
Figure 8C:
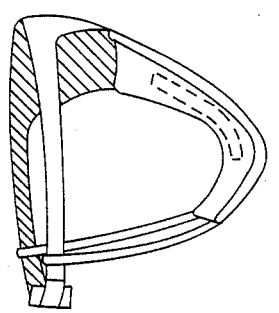

FIGS. 8a-8c show another embodiment of the anal pad according to the present invention which is provided with waistband 11 and supporting straps 13. In FIG. 8a, element 9 is the male version of the anal pad as discussed above. Element 10 is a band made of gauze, lignin or other suitable material and is connected to the wider end of anal pad 9. Extending from one side of band 10 is waistband 11, and extending from the other side of band 10 is a strip of adhesive material, for example, a combination of glue and paper. As shown in FIG. 8b, waistband 11 is attached around the waist of the user and held in place by adhesive material 12.

Extending from the thinner end of anal pad 9 are two attachment strips which also have strips of adhesive material extending therefrom. As similarly shown in FIGS. 8b and 8c, strips 13 are brought upward and are attached within waistband 11 by adhesive strips 12.

Figure 9:
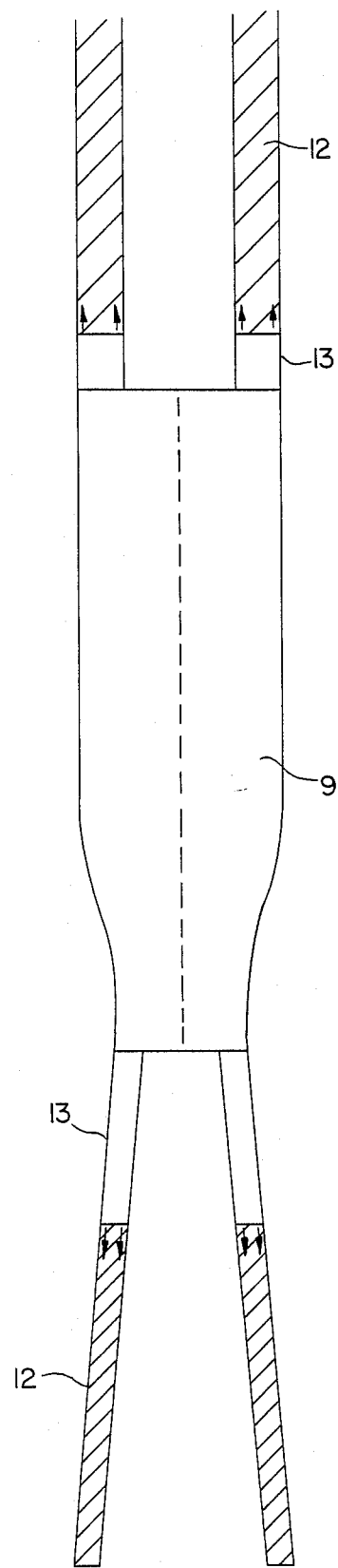
FIG. 9 shows another embodiment of the present invention.

FIG. 9 shows still another embodiment of the anal pad in which four attachment strips extend from the corners of anal pad 9. Attachment strips 13 extend into strips of adhesive material 12 which are used to attach the pad to the underwear of the user. This embodiment is similar to the embodiment of FIGS. 1-6 in which a layer of adhesive 8 is used to attach the anal pad to the inside of the underwear of the user.

Figure 10A:
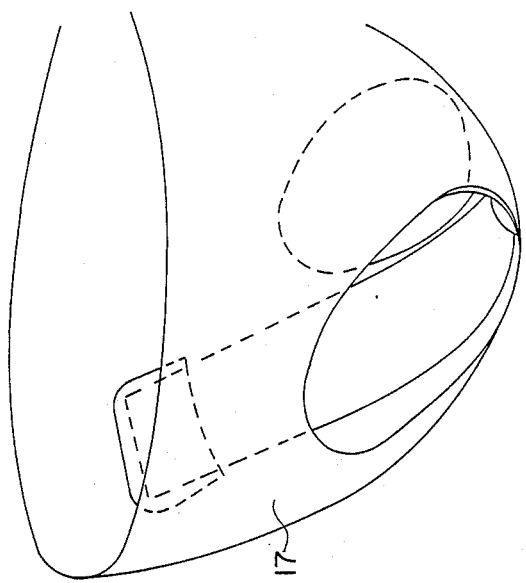
FIGS. 10a–10c show a further embodiment of the present invention.
Figure 10B:
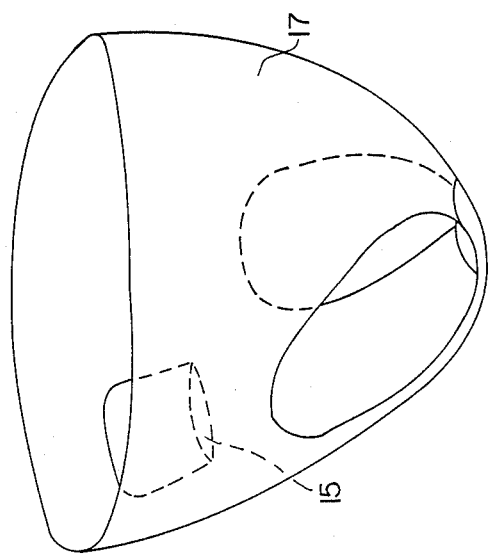
Figure 10C:
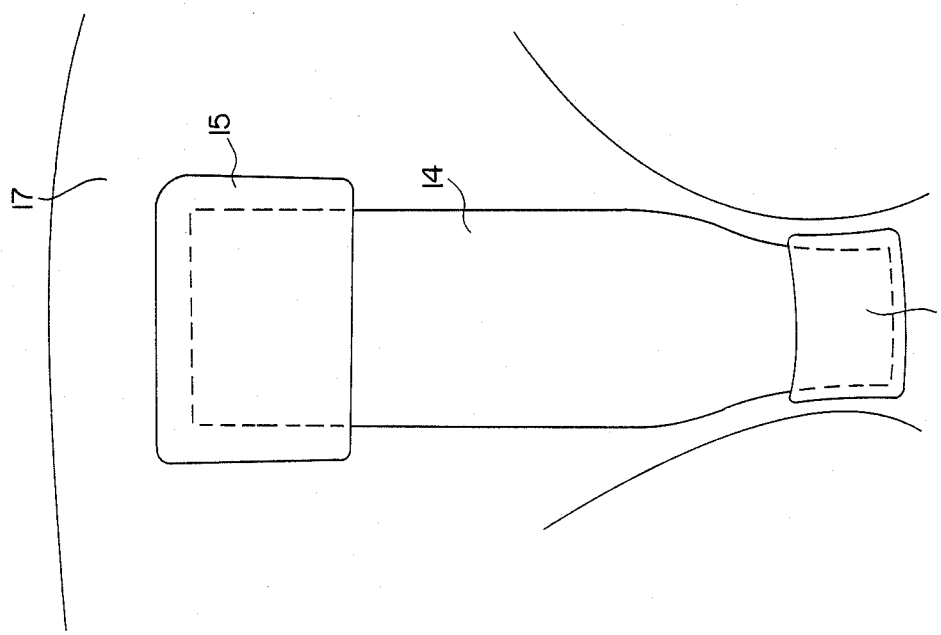

FIGS. 10a-10c show underwear adapted to be used with an anal pad according to the present invention. This underwear may be either regular or special elastic underwear in which pockets are sewn or attached by other means. Anal pad 14 fits within posterior pocket 15 and interior pocket 16 on the inner side of underwear 17.

The embodiments of the anal pad discussed above are shown to be excellent with regard to eliminating sound, odor and soiling effects. Each pad provides between 3-12 hours of full protection depending on the thickness of the pad and the severity of the symptoms.

This invention has been described in detail in connection with the preferred embodiments. The preferred embodiments, however, are merely for example only and this invention is not restricted thereto. It will be easily understood by those skilled in the art that variations and modifications can be easily made within the scope of the invention, as defined by the appended claims.

We claim:

1. An anal pad comprising:
    an outer shell having an interior surface;
    a semi-rigid inner shell enclosed within said outer shell and fully lining an interior surface of said outer shell along a first side of said outer shell adapted to be adjacent to a user's undergarment and partially lining an interior surface of a second side of said outer shell opposite said first side and adapted to be adjacent to the user's anus so as to form a central slot in said outer shell; and
    an absorbing layer located within said semi-rigid inner shell and filling the interior space of said anal pad and supporting said semi-rigid linings in spaced apart relationship to form a sound reflecting chamber, said absorbing layer trapping fecal matter and absorbing the odor of gas expulsed from the anus by flatus, and trapping the sound of flatus.

2. The anal pad recited in claim 1 wherein said absorbing layer contains a deodorant including glycerin.

3. The anal pad recited in claim 2 further comprising an adhesive on an exterior surface of said first side of said outer shell which is covered by a removable thin sheet.

4. The anal pad recited in claim 3 wherein said absorbing layer is made of any light and porous material including cotton and rayon fiber.

5. The anal pad recited in claim 3 wherein said outer shell comprises a thin layer of lignin paper and said semi-rigid inner shell is comprised of a plurality of layers of compressed paper.

6. The anal pad recited in claim 3 further comprising a thin layer of lining paper between said absorbing layer and said semi-rigid inner shell, said thin layer enclosing said absorbing layer.

7. The combination of an anal pad and an undergarment comprising:
    an anal pad having an outer shell, semi-rigid inner shell enclosed within said outer shell and lining at least the interior surface of said outer shell adjacent to the undergarment but not the surface of the outer shell adjacent to the anus, and an absorbing layer located within said outer shell; and
    said undergarment comprising a posterior pocket located on the back end of said undergarment and an interior pocket located at the bottom of said undergarment in which said anal pad is retained, wherein, said inner shell reflects the sound of a flatus off of its interior surface, and said absorbing layer traps fecal matter and the odor of gas expulsed from the anus by a flatus, and traps the sound of a flatus.

* * * * *